United States Patent

Familletti

[11] Patent Number: 4,649,117
[45] Date of Patent: Mar. 10, 1987

[54] AIR LIFT BIOREACTOR

[75] Inventor: Philip C. Familletti, Millington, N.J.

[73] Assignee: Hoffmann-La Roche Inc., Nutley, N.J.

[21] Appl. No.: 711,932

[22] Filed: Mar. 15, 1985

[51] Int. Cl.[4] .............................................. C12M 1/04
[52] U.S. Cl. ................................... 435/313; 435/241
[58] Field of Search .............. 435/313, 314, 240, 241, 435/243, 284-286

[56] References Cited

U.S. PATENT DOCUMENTS

| | | | |
|---|---|---|---|
| 3,649,465 | 3/1972 | Scharf et al. | 195/143 |
| 4,036,693 | 7/1977 | Levine et al. | 435/241 |
| 4,085,007 | 4/1978 | Hawkins | 435/313 |
| 4,204,042 | 5/1980 | Chelle | 435/314 |
| 4,208,483 | 6/1980 | Lee | 435/313 |
| 4,259,449 | 3/1981 | Katinger et al. | 435/241 |
| 4,311,798 | 1/1982 | Katinger et al. | 435/286 |
| 4,337,315 | 6/1982 | Fukushima et al. | 435/313 |
| 4,545,945 | 10/1985 | Prave et al. | 435/314 |

FOREIGN PATENT DOCUMENTS 1426975 12/1965 France .
2133355 11/1972 France .
0179495 10/1983 Japan .................... 435/241

OTHER PUBLICATIONS

Feder et al., The Large-Scale Cultivation of Mammalian Cells, (1983), pp. 36-43, Scientific American 248, No. 1.
Onken et al., Airlift Fermenters: Construction, Behavior, and Uses, (1983), pp. 67-95, Advances in Biotechnological Processes 1.

*Primary Examiner*—Samuel Scott
*Assistant Examiner*—Noah Kamen
*Attorney, Agent, or Firm*—Jon S. Saxe; George M. Gould; Mark E. Waddell

[57] ABSTRACT

The disclosure provides an improved reactor/fermentor apparatus useful for carrying out cell culture and fermentation. The apparatus utilizes novel design features to provide optimum agitation of the cells while minimizing mechanical shear force. The reactor is composed of two chambers; an upper, wider chamber and a lower, small diameter chamber which are connected by inwardly sloping side walls. Agitation is accomplished by utilizing a gently flowing centrally disposed gas stream.

12 Claims, 5 Drawing Figures

CELL BIOREACTOR

CELL BIOREACTOR

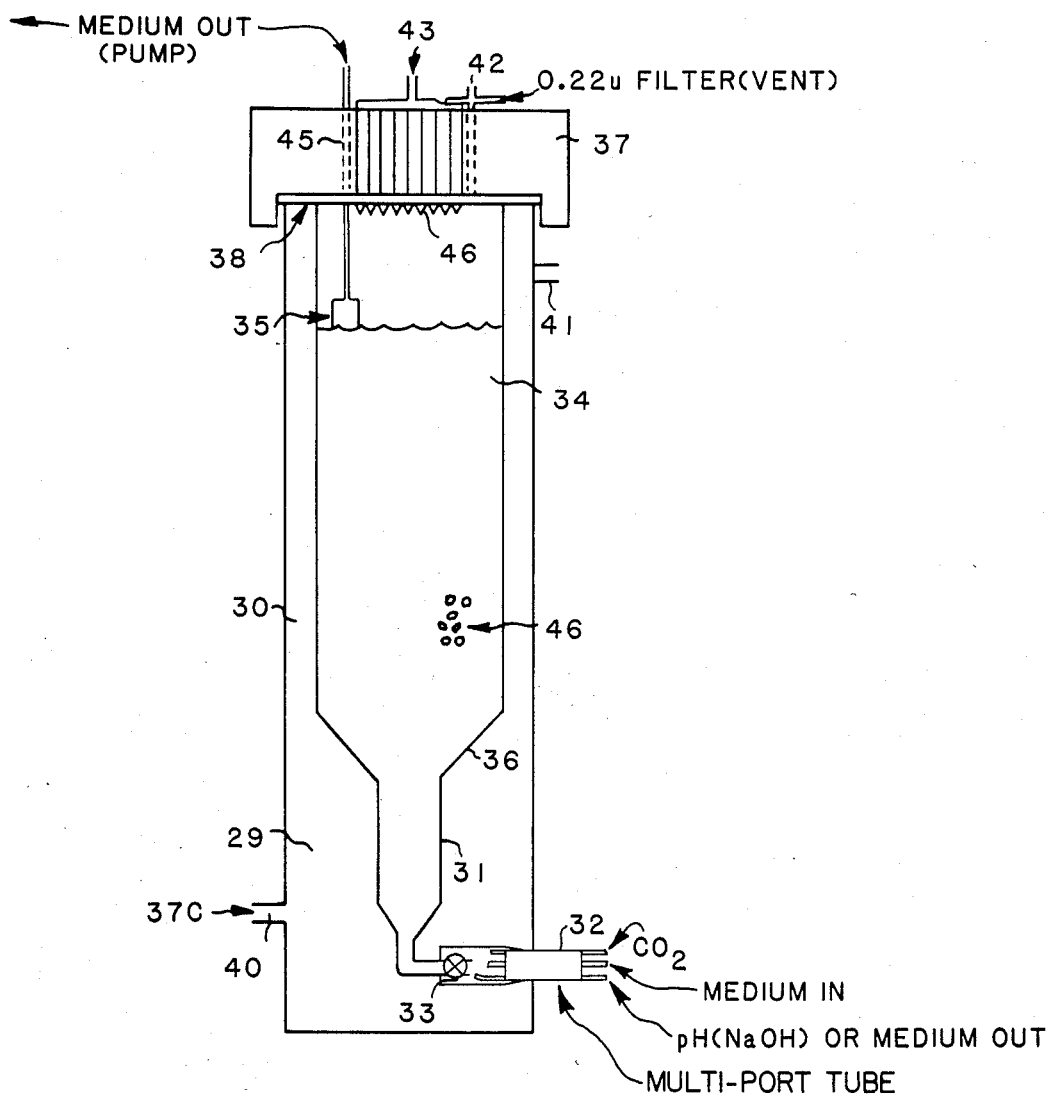

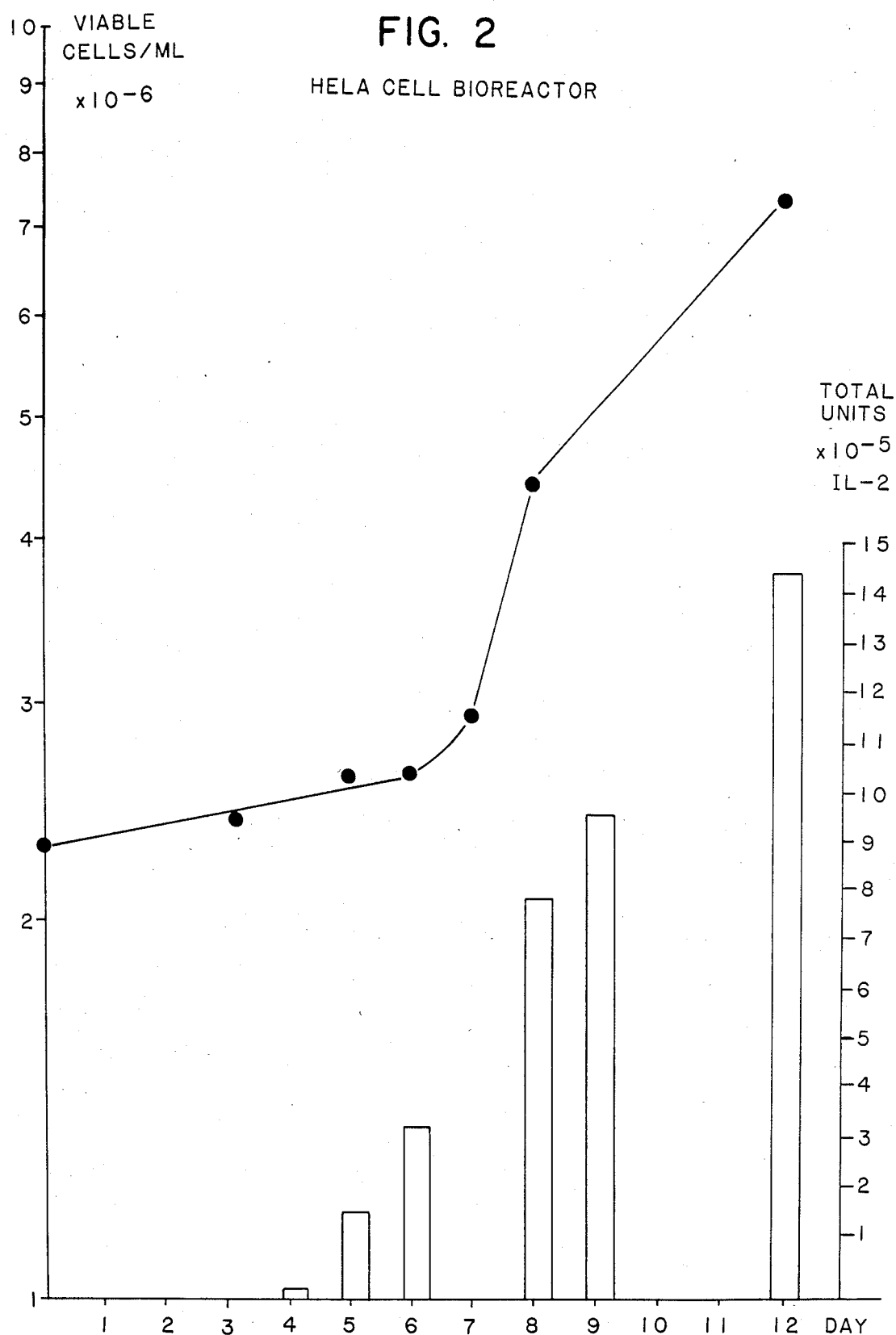

AIR LIFT BIOREACTOR

SUMMARY OF THE INVENTION

The present invention relates to an improved reactor/fermentor apparatus useful for carrying out cell culture and fermentation. The apparatus of the present invention utilizes design features which afford optimum agitation of the cells with a minimum mechanical shear force. This is accomplished by utilizing a gas stream to provide gentle aeration. The design provides gentle agitation without the need to employ any mechanical parts which might damage cells or cell carriers.

The reactor of the present invention is composed of two chambers; an upper wider chamber which is designated the growth chamber and a lower, smaller diameter chamber which is designated the mixing chamber. In a preferred embodiment, the reactor may be constructed within a fluid temperature bath to provide constant temperature during the entire cell culture procedure. Further embodiments provide for use of the reactor in either suspension or cell carrier culture. Moreover, the unit may be employed either as a reactor or as a fermentor and thus can be employed to grow eukaryotic or prokaryotic cells.

DESCRIPTION OF THE DRAWINGS

FIG. 1A is a frontal, schematic representation of an alternate embodiment of the reactor of the present invention wherein the cover of the reactor is adapted to provide a multi-head gel ball maker for immobilizing cells to be cultured. Similarly, the reactor of this embodiment is provided with a multi-port inlet at the bottom of the reactor vessel to allow input or output of various gas or liquid streams during the course of the reaction.

FIG. 2 is a graphic representation of a eukaryotic cell culture in a bioreactor of the instant invention. The graph provides an indication of viable cells found at the appropriate phase of the culture and an indication of the total units of product (human IL-2) produced by the cells.

DESCRIPTION OF THE INVENTION

Figure 1:
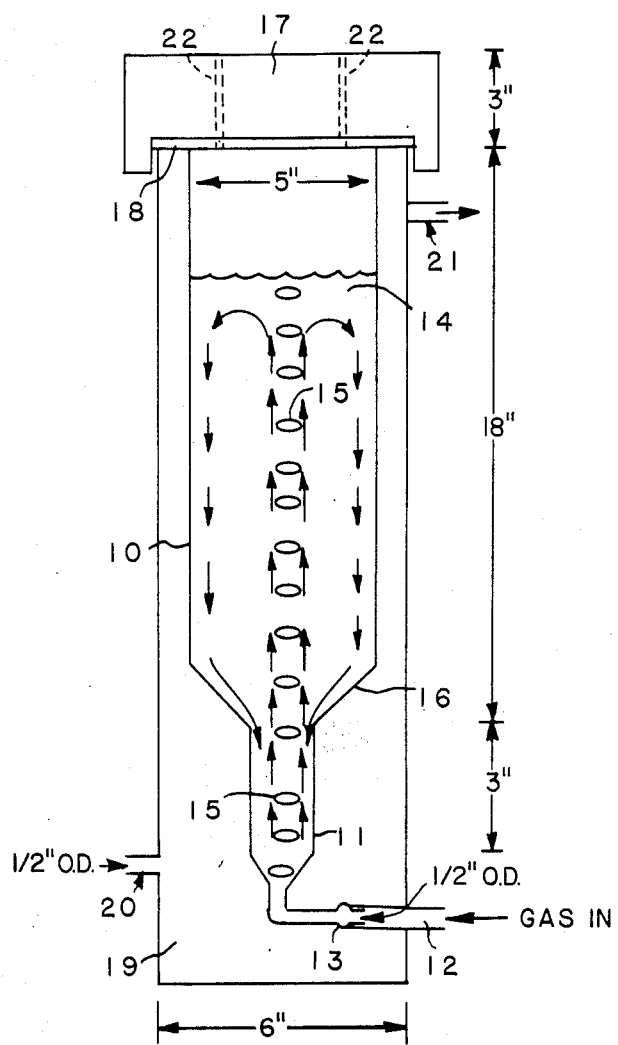
FIG. 1 shows a frontal, schematic representation of a bioreactor of the present invention with arrows and small circles designating the typical flow pattern of cells within the media partially filling the reactor.

The novel reactor/fermentor apparatus of the present invention can be more readily understood by reference to FIG. 1 of the Drawings. As seen in such figure, the reactor is composed of two chambers: an upper chamber numeral 10 of relatively larger dimension and a lower chamber 11 of relatively smaller dimension. The upper chamber functions as a growth chamber while the lower chamber is designated the mixing chamber. A gas inlet line 12 communicates through valve means 13 to the bottom of mixing chamber 11. In operation, air, $CO_2$ or other appropriate gas or gas mixture is gently bubbled through the lower port provided by inlet means 12. As the gas rises through the fermentation of cell culture medium 14 contained within the chambers it displaces liquid in the lower portion of chamber 11 and carries cells, designated by the small circles 15, upward as indicated by the upward pointing arrows. Media from the upper portion of the reactor moves downward and sweeps over the slanted floor 16 to replace the displaced medium at the bottom of chamber 11. This is indicated by the downwardly moving arrows in FIG. 1. Suitable gas flow rates to achieve the desired cell suspension are in the range of about 10 to 300 cc/min preferably from about 25 to 50 cc/min.

In this manner there is set up a cyclic movement in the upper reactor chamber 10 keeping the cells or cell carriers in suspension. This also keeps the dissolved oxygen concentration in the medium high enough for optimum cell growth. In a preferred embodiment a gas comprising air with about 5% $CO_2$ is used. The addition of this minor amount of carbon dioxide to the input gas helps to maintain a proper pH for the culture medium. Only a very gentle bubbling is needed to create the lift necessary to keep cells in suspension. Such gentle bubbling action minimizes shear forces and foaming of the medium at the medium surface.

Size dimensions provided are for illustrative purposes only and are not narrowly critical. For larger volumes, the diameter of the upper and lower chambers can be increased proportionally. The overall height of the reactor may be increased without a change in diameter. For small volumes of cell cultures, the dimensions of the reactor can be scaled down proportionately.

The reactor may be fabricated from glass, stainless stel, or other suitable material that is not toxic to cell viability and can desirably withstand sterilization. In similar fashion the reactor lid 17 is fabricated from a dense plastic with preferably can withstand sterilization conditions, e.g. autoclaving. Since it is a separate piece, it can be modified to provide versatility in the use of the reactor as will be seen in further embodiments of the present invention. Sterility is maintained by a gasket 18 which is made of a flexible material such as rubber and is fitted at the base of the lid. This material forms a seal with the upper portion of the reactor and may be held or clamped in place by any suitable means such as by the weight of the lid. The reactor shown in FIG. 1 is kept at constant incubation temperature by means well known in the art such as, for example by perfusing a heated fluid, e.g. water, into the external reactor chamber 19 which surrounds the reactor via inlet 20. Circulation of the heating fluid can be achieved by means of a circulating heat pump not shown. The heating fluid is circulated out of the jacket chamber 19 by means of outlet 21 and can be recycled through the external pump and heating means for return to the system at the desired temperature. For most cell culture and fermentation applications, the preferred temperature of operation is 37° C. It should be noted that this use of an external heating jacket is optional. Heating can also be achieved in the absence of the jacket by placing the entire reactor in an incubated chamber or hot room at 37° C.

Prior to use, the reactor and lid are preferably steam sterilized separately and asceptically assembled or steam sterilized in place, or sterilized assembled by filling the inner chambers and tubing with an appropriate sterilization media, such as 70% ethanol or a 1% sodium hypochlorite solution.

Build up of excess gas pressure is avoided by using appropriate filtered—(0.22μ) vent lines 22 in the lid 17. The lid may also be adapted to contain inlet and outlet lines for the addition of media. Alternatively it is possible to utilize a multi-port tube as a part of inlet means 12 to allow not only the introduction of the gas stream from the bottom of the reactor vessel but also the media and any needed solutions required to buffer or maintain pH at desired levels. Such embodiments are shown in FIG. 1.

The bioreactor of FIG. 1 is particularly useful in carrying out suspension cell fermentation. In such procedure, cells are seeded in growth medium at a concentration of proximately $1 \times 10^5$ cells/ml. A mixture of 5% $CO_2$ and 95% air is gently bubbled through the medium. At optimum cell density a portion of the medium containing cells is removed and fresh growth medium devoid of cells is added. This procedure maintains the cells in log phase. Cells or cell product are continuously harvested. The bioreactor was able to maintain growth and viability or hybridoma cell lines (monoclonal antibody producing cells such as LI-8 providing monoclonal antibody against leukocyte interferon) and cells which produce bioactive proteins such as the KG-1 cells producing interferon. Each cell line maintained viability over an extended time period and was able to elicit the product which can be harvested from the cell media.

In similar fashion it is possible to utilize other cell systems in conjunction with the reactor of the present invention. Such other cells include Jurkat, a human T cell derived cell line which upon induction produces human interleukin 2; Hela cells, which are a human carcinoma cell line which are transfected with the gene for human interleukin 2; and C 1271, a murine mammary tumor which is transfected with the gene for human interleukin 2. Other cell systems employable in conjunction with the present invention include transformed microorganisms which contain genes for human proteins and which are capable of secreting the gene products into the media. Such cells include yeast, B. subtilis and the like.

Other cell systems require solid supports in order to grow. These anchorage dependent cells can be conveniently grown in culture by utilizing a modification of the present cell reactor. Thus in FIG. 1A there is provided a fermentor/bioreactor which provides a suitable device for the growth of anchorage dependent cells, which cannot be adapted to grow in suspension. In such embodiment the upper chamber and lower chamber of the reactor 30 and 31 respectively may be of the same dimensions and configuration as in the reactor vessel described in FIG. 1. As in the previous design the two chambers are joined by slanted walls 36. This facilitates the circulation of cells or cell carriers, within the media with low air flow so as to provide requisite agitation without any substantial shear force.

A multi-port tube 32 provides inputs for the air stream, inflow of media and any buffer for moderation of pH. The inflow passes through valve 33 into the bottom of mixing chamber 31. The reactor is provided with an optional temperature control jacket 29 which contains fluid inlet means 40 and fluid outlet means 41. Media can be continuously removed from the reactor by means of media outlet line 45 which extends down to the upper surface of the reactor media 34. A mesh screen 35 is provided at the outlet head in order to prevent clogging of the outflow of the suspension cell particles.

Anchorage dependent cells which cannot be adapted to grow in suspension may be grown in the reactor of this embodiment by seeding these cells at approximately $1 \times 10^5$ cells/ml in the upper chamber 30. This chamber may be modified to contain means to increase the surface area for attachment. Such means may include any of the commercially available microcarriers, e.g., honey-combed ceramic blocks, bundles of thin fibers or hollow fibers, or other devices which provide a suitable substrate for cells to attach and grow. The reactor configuration is particularly suitable for microcarriers because of the low shear force and excellent agitation provided by the airlift. Devices which increase surface area need an increased concentration of dissolved oxygen and constant profusion of fresh medium to maintain viability of the dense cell culture. This embodiment of the reactor provides both these parameters.

In the embodiment depicted the attachment cells are adapted to grow in a semi-solid substrate such as sodium alginate; agarose; agar; carrageenan; gelatin or others. In operation one part of the cell suspension of the cell line which requires attachment is mixed with two parts of a 1.5% alginate solution (1% final). The mixture is then dripped through the reactor vessel lid 37 via inlet 43 and capillaries 46 into the reactor which contains a solution of aqueous $CaCl_2$ (50 mM). The calcium solution serves to polymerize the alginate trapping the cells in small balls as indicated by 46. These gel balls containing the cells are rinsed free of the $CaCl_2$ and resuspended in growth medium. The entire procedure as indicated can be performed in a reactor equipped as indicated with the modified lid design. As in the prior embodiments the lid is maintained in air tight relation with the reactor vessel by means of rubber gasket 38. Excess gas pressure can be vented through vent line 42. If desired a suitable filter can be employed to maintain sterility of the reactor.

Examples of a suitable cell line which are attachment dependent are Hela cells which have been transfected with a gene for human interleukin 2. The Hela cells were cultured in the reactor for 12 days before the run was terminated. These cells in this demonstration run reached a concentration 7-fold higher than can be obtained by conventional cell culture. The interleukin 2 produced by the cells was measured and the results of the experiment are shown in FIG. 2. As can be seen, interleukin 2 was continuously released into the medium as shown by the bars.

Figure 3:
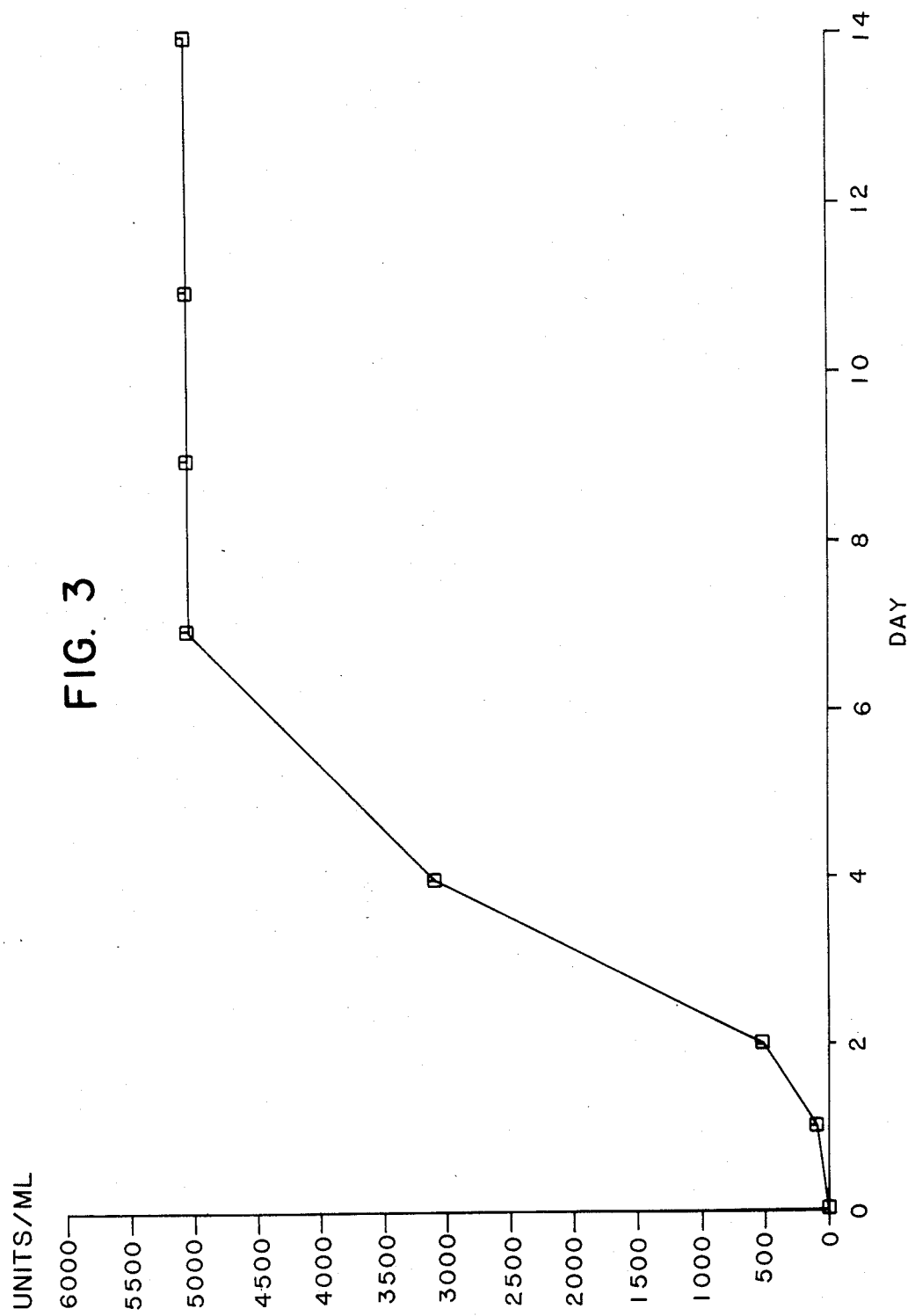
FIG. 3 provides a graph showing the results of a cell culture with a murine mammary tumor cell line transfected with the gene for human IL-2. This culture employed alginate gel balls to immobilize the cells during culture. Activity values for human IL-2 found in the culture medium on the indicated culture days is presented in the graph.

In a further demonstration of the advantages derived by employing the modified bioreactor of the present invention; C1271 cells, a murine mammary tumor which had been transfected with a gene for human interleukin 2 were employed. These cells constitutively produce human interleukin 2. C1271 cells were immobilized at a concentration of $4 \times 10^5$ cells/ml in 1% alginate as described above. The alginate gel balls and the bioreactor were aerated with a 5% $CO_2$ and 95% air mixture (v/v) and perfused with growth medium at a constant rate. The immobilized cells were maintained in culture for 14 days. A concentration of 5,000 units/ml of interleukin 2 was continuously collected for 7 days from the profusion culture medium (FIG. 3). This is a 10-fold increase in yield of IL-2 obtained from the same cells when grown by conventional monolayer culture.

Figure 4:
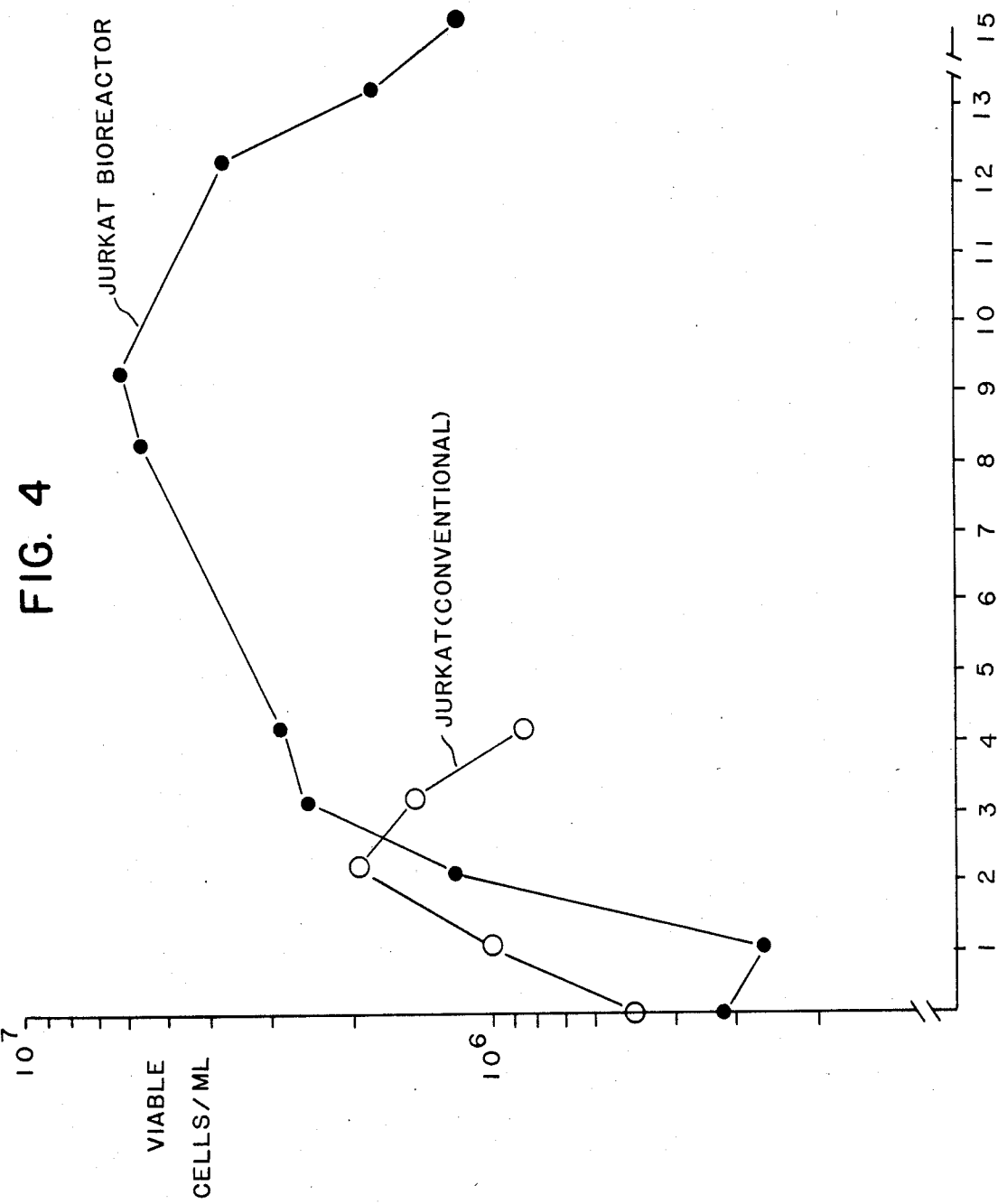
FIG. 4 is a comparison of a Jurkat cell culture utilizing either conventional cell culture techniques or using alginate immobilized cells grown in cell culture in a bioreactor embodiment of the present invention. The graph provides the total number of viable cells which were found during the course of the culture.

In yet another embodiment of the present invention, Jurkat cells were prepared in alginate balls identical to the methods employed above. Growth medium was perfused at a rate of 0.5 m/min. through the multi-port tube 32. Results of the experiment are summarized in FIG. 4. The viability of the Jurkat subculture was maintained for 15 days before termination of the run. These cells reached a density of approximately $8 \times 10^6$ cell/ml. Similar cells seeded in a conventional 1-liter spinner culture reached a density of $2 \times 10^6$ cell/ml. Cells in this conventional culture maintained viability for only 4 days.

I claim:

1. A bioreactor/fermentor which maintains cells or immobilized cells in suspension and whose geometry provides a mixing action to said cells with gentle aeration with a minimum of shear force, said bioreactor/fermentor comprising, a reactor vessel having a mixing chamber with a lower end and an open upper end, and a growth chamber with an open lower end located above said mixing chamber, wherein the open upper end of said mixing chamber and the open lower end of said growth chamber coincide with one another;

said mixing chamber having a first cylindrical side wall which defines the open upper end, a centrally located gas inlet means located in the lower end of said mixing chamber, and a bottom attached to the first cylindrical side wall of sealing the bottom of the reactor vessel, for receiving the gas inlet means and, together with the first cylindrical side wall, for defining the lower end of said mixing chamber; and said growth chamber comprising a conical side wall defining the open lower end of said growth chamber, the conical side wall sloping inwardly toward the open upper end of said mixing chamber, a second cylindrical side wall of larger diameter than the first cylindrical side wall of said mixing chamber, the second cylindrical side wall being located above the conical side wall, and top lid means for providing an air tight seal on said growth chamber, the top lid means including gas vent means, whereby oxygen containing gas may be introduced into said reactor vessel through the centrally located gas inlet means and bubbled up through the cells and liquid medium to gently carry the cells and liquid medium upward from said mixing chamber to said growth chamber and the cells and liquid medium in said growth chamber flow downward along the conical side wall sloping inwardly towards the open upper end of said mixing chamber to replace the cells and liquid medium being carried upwards from said mixing chamber by the oxygen containing gas, thereby providing a mixing action to said cells with aeration and a minimum of shear force while providing dissolved oxygen in the medium to support cell growth.

2. The bioreactor of claim 1 wherein said reactor vessel is supported within a temperature control jacket means having fluid inlet and fluid outlet means.

3. The bioreactor of claim 1 wherein said lid means is arranged and constructed to comprise a means for forming microcarriers for cell immobilization.

4. The bioreactor of claim 3 wherein said gas inlet means comprises a multi-port tube adapted to provide inlet means for gas, medium and pH adjusting solution.

5. The bioreactor of claim 3 wherein said lid means further comprises a medium outlet means.

6. A method for carrying out cell culture or fermentation in a reactor vessel having a cylindrical mixing chamber with an open upper end and a cylindrical growth chamber of larger diameter than the mixing chamber, the growth chamber having a downward sloping conical sidewall defining an open lower end coinciding with the open upper end of the mixing chamber, wherein the cells and the growth medium are gently circulated between the mixing chamber and growth chamber without any need for internal baffles and the liquid growth medium is aerated to provide sufficient oxygen to support cell growth while subjecting the cells to a minimum amount of shear force, said method comprising the steps of:

(a) introducing a liquid growth medium into the reactor vessel to fill the mixing chamber and the growth chamber of the reactor vessel;

(b) introducing a cell or immobilized cell population into the growth medium in the reactor vessel;

(c) introducing a gentle stream of oxygen containing gas into the center of the mixing chamber and bubbling the oxygen containing gas upwardly from the mixing chamber into the growth chamber at a flow rate between about 10 to 300 cc/minute which is sufficient to lift cells and liquid growth medium from the mixing chamber up into the growth chamber, maintain the cells in suspension and to aerate the liquid growth medium thereby providing sufficient oxygen to support cell growth;

(d) recirculating upwardly lifted cells and liquid growth medium from the growth chamber back to the mixing chamber while passing the cells and liquid growth medium across the downward sloping conical sidewall of the growth chamber to sweep cells and liquid growth medium off of the conical sidewall of the growth chamber; and (e) growing the cells while maintaining the liquid growth medium and cells at a preselected incubation temperature.

7. The method of claim 6 wherein said cells are eukaryotic or prokaryotic.

8. The method of claim 6 wherein said incubation temperature is about 37° C.

9. The method of claim 6 wherein said cells grow in suspension.

10. The method of claim 9 wherein said cells are anchorage dependent and are supported by microcarriers.

11. The method of claim 6 wherein said microcarriers comprise gel balls immobilizing said cells.

12. The method of claim 6 wherein said gas stream comprises about 5% $CO_2$ and 95% air.

* * * * *